United States Patent

Hayes et al.

[11] Patent Number: 5,945,344
[45] Date of Patent: Aug. 31, 1999

[54] ELECTROCHEMILUMINESCENCE METHOD

[75] Inventors: Stephanie A. Hayes, Gaithersburg; Jonathan K. Leland, Silver Spring; David B. Talley, Olney, all of Md.

[73] Assignee: Igen International, Inc., Gaithersburg, Md.

[21] Appl. No.: 08/986,709

[22] Filed: Dec. 8, 1997

Related U.S. Application Data

[63] Continuation of application No. 08/474,176, Jun. 7, 1995, abandoned.

[51] Int. Cl.⁶ ................................................ G01N 21/76
[52] U.S. Cl. ........................ 436/172; 422/52; 250/361 C
[58] Field of Search .............................. 422/52; 436/172; 250/362, 361 C

[56] References Cited

U.S. PATENT DOCUMENTS

| | | | |
|---|---|---|---|
| 5,061,445 | 10/1991 | Zoski et al. | 422/52 |
| 5,147,806 | 9/1992 | Kamin et al. | 436/172 |
| 5,315,993 | 5/1994 | Alcala | 422/82.07 |
| 5,527,710 | 6/1996 | Nacamulli et al. | 436/517 |
| 5,672,515 | 9/1997 | Furlong | 436/172 |

*Primary Examiner*—Jeffrey Snay
*Attorney, Agent, or Firm*—Whitman Breed Abbott & Morgan LLP

[57] ABSTRACT

The invention is a method for conducting an electrochemiluminescent assay that includes contacting a sample containing an analyte of interest with a first electrical waveform, followed by contacting the sample with a second electrical waveform that has been modulated in an amount derived from a pre-determined gain extension factor.

50 Claims, 6 Drawing Sheets

ELECTROCHEMILUMINESCENCE METHOD

This application is a continuation of application Ser. No. 08/474,176, filed Jun. 7, 1995, now abandoned, which is incorporated herein by reference.

TECHNICAL FIELD

The invention involves improved chemiluminescence methods, particularly, electrochemiluminescence (ECL) detection methods.

BACKGROUND OF THE INVENTION

Chemiluminescence is the generation of light as a product of certain chemical reactions, typically conducted at ordinary or room temperature. These reactions typically produce a reaction intermediate in an electronically excited or active state; the radioactive decay of the excited state to the ground state is the source of visible light, or luminescence in the form of visible light, ultraviolet, or infrared radiation. Most importantly, the formation of electronically excited reaction products can be detected by measuring the luminescence intensity, even when the radiation is minimal or negligible.

Most chemiluminescent reactions can be classified into (1) peroxide decomposition, such as bioluminescence or peroxyoxalate chemiluminescence; (2) singlet oxygen chemiluminescence; and (3) ion radical or electron transfer chemiluminescence, such as electrochemiluminescence. In principle, one molecule of a chemiluminescent reactant can react to produce one electronically excited molecule, which in turn can emit one photon of light. Light yields can therefore be defined in the same terms as chemical product yields, i.e., in units of einsteins of light emitted per mole of chemiluminescent reactant.

Electrogenerated chemiluminescence, alternatively referred to as electrochemiluminescence (ECL), is an electrochemical means for converting electrical energy into light. With ECL processes, controlling the electrode potential is an extremely powerful control mechanism for modulating the rate of light generating reactions, a characteristic that provides certain advantages over chemiluminescence or bioluminescence methods. For example, ECL has been used with great success to image the heterogeneity electron-transfer rates at electrode surfaces with submicrometer spatial resolution.

ECL systems and devices typically use solutions of luminescent molecules, i.e. molecules which upon electrical excitation are capable of emitting ECL, such as luminol, ruthenium tris (2,2'-bipyridine) dichloride hexahydrate [Ru(bpy)$_3$Cl$_2$•6H$_2$O], or Ru(bpy)$_3^{2+}$. ECL processes have been demonstrated for many different molecules by several different mechanisms. For example, in one of the many electrochemiluminescence reactions, alternating current may be used to excite hydrocarbon radicals. The reaction intermediates, anions and cations, are continuously formed and destroyed, and in doing so, release radiant energy. It is believed that the energy released as a product of an electron transfer process produces the light. Since the lifetimes of excited luminol and Ru(bpy)$_3^{2+}$ are on the microsecond time scale, the excited molecules cannot diffuse more than a few hundred nanometers before emitting their photons.

ECL has been developed as a highly sensitive process in which reactive species are generated from stable precursors (i.e., the ECL-active label) at the surface of an electrode. This technology has many distinct advantages over other detection systems: no radioisotopes are used; detection limits for the label are extremely low (200 fmol/L); the dynamic range for label quantification extends over six orders of magnitude; the labels are extremely stable compared with those of most other chemiluminescent systems; the labels, small molecules (~1000 Da), can be used to label haptens or large molecules, and multiple labels can be coupled to proteins or oligonucleotides without affecting immunoreactivity, solubility, or ability to hybridize; because the luminescence is initiated electrochemically, selectivity of bound and unbound fractions can be based on the ability of labeled species to access the electrode surface, so that both separation and nonseparation assays can be set up; and measurement is simple and rapid, requiring only a few seconds.

A typical ECL cell includes a first electrode and a second electrode, a first compound capable of generating ECL, a second compound capable of reacting with the first compound to generate ECL, and a source of supply of an electrical potential between the electrodes. In conventional ECL devices, the luminophores are homogeneously distributed in solutions, a fluidic pathway, or polymer films, or the active constituents (i.e., the luminescent molecules) may be confined to the surface of the electrodes as immobilized layers.

As an electrical potential is supplied to the first electrode, the first compound is electrolyzed to produce a species, a reaction intermediate, that reacts with a second compound (dissolved in a solution) to generate ECL. The ECL emission from the luminophore can be easily detected and is very intense with some electrode materials. The intensity of the luminescence increases with the applied voltage until the reactant species at the surface of the electrode is depleted, resulting in decreased intensity. The intensity of the observed luminescence is great enough that it can easily be measured with conventional transducers, such as a photomultiplier tube (PMT), operating either in photon-counting or current modes.

ECL may be used in a wide variety of detection protocols. For example, immunoassays have been readily demonstrated and developed into a wide range of different formats. Nonseparation competitive assays of haptens can be formatted by using a labeled hapten that competes for antibody with the analyte. Competitive assays for either haptens or large molecules can also be formatted as solid-phase assays. Microparticles coated with antigen compete with the analyte for labeled antibody. This assay format can be used for either large analytes or haptens. Solid-phase sandwich immunoassays can also be formatted by using two antibodies specific for different epitopes of the analyte. These solid-phase assays can be formatted as either separation or nonseparation assays. DNA probe assays can also be performed with use of ECL to detect hybridization of labeled probes to nucleic acid sequences. All such measurements typically require the use of a luminometer, if the sample is in a liquid, or an imaging device, if the light is emitted from a two-dimensional sample, e.g. a membrane used in blotting.

The luminometer is designed to measure small amounts of light, usually in the visible spectrum. The sample is presented in a cuvette, the volume of sample being usually between 100 and 500 µl and the cuvette (usually 10–12 mm diameter and about 40–75 mm long and disposable, being made from polycarbonate or similar transparent plastic) capable of holding up to 3 ml. Light is detected by a photomultiplier or by a solid state photodiode. Signals from the detectors may be either current or photon-counts. The instrument may have the capability to handle automatically many samples in a programmed or programmable fashion._

Instruments may be fitted with automatic injectors so that several reagents may be added to the sample during the course of processing. A few instruments have temperature control for the sample and some incorporates a temperature compensation factor to correct the result. Most units are fitted with a RS232 port so that the luminometer may be connected to, and in some instances controlled by, an external computer.

ECL processes exhibit an extremely wide response in intensity to luminophore concentration ranges. The typical range is about $10^6$ to about $10^7$ counts. To provide proper results, the luminometer detection range preferably equals or exceeds the range for the ECL process (and assay range). Commercially available luminometers, typically provided with one gain setting, are not always capable of meeting the necessary range. If the sample intensity is over-range (greater than the range for the luminometer, e.g., greater than $10^7$ counts) or under-range (to little), the reading is lost and must be re-run, costing time and reagent expense. Since one reading per sample is generated, if a reading goes off-scale it cannot be determined unless the run is repeated successfully at a lower luminometer gain or sample dilution. Furthermore, conventional ECL protocols using conventional equipment are typically a compromise between the low end amount of luminescence and the high end, since the luminometer has a fixed range at only one gain setting.

Thus, there is a need to improve the dynamic range for ECL detection and to eliminate the need for repeating the process.

SUMMARY OF THE INVENTION

The present invention provides a method and apparatus for determining the concentration of a sample when its intensity is outside the dynamic range of the instrument's luminometer and at a point in the process which permits the operator to obtain the needed information without re-running the ECL reaction.

The technique provides an easy method for the instrument to accommodate the extremely wide dynamic range of ECL luminophores. Furthermore with this technique, a simpler and cheaper luminometer design can be incorporated into the ECL instrument. Also, a higher luminometer gain may be used in cases where it is needed for assay sensitivity, without loss in the upper end range.

A characteristic of ECL processes is that the electrode voltage can be used to modulate the ECL reactions. This provides the opportunity for accelerating or slowing the light generation processes. The light can be turned off and on, with intermittent delays. Further, by proper selection of electrode voltage waveform, the light output can be held relatively constant (DC) or made to oscillate (AC). This technique will eliminate the necessity to re-run the sample at a lower luminometer gain or after sample dilution.

Some of the advantages of the ECL techniques according to the present invention include the following:

The method involves no radioisotopes, eliminating disposal and lifetime problems inherent in radioimmunoassays.

ECL provides for extremely sensitive label detection at subpicomolar concentrations, as well as an extremely wide dynamic range of greater than six orders of magnitude.

At one gain setting, for example a high gain setting in order to detect low concentrations, all values of intensity over an extremely wide range may be determined. Typically, an intensity range of about $10^9$ counts may be achieved.

The metal-ligand labels are extremely stable, having shelf lives of longer than one year at room temperature. Labeled proteins are similarly stable if stored at 2–5° C.

The label is extremely versatile: it can be chemically activated with several different reactive groups to provide for easy labeling of haptens, antibodies, and nucleic acids as well as other molecules.

Because of the label's low molecular mass and its hydrophilicity, immunoglobulins can readily be labeled with >20 label molecules per antibody without affecting antibody solubility or immunoreactivity. Similarly, the label does not affect the specificity or hybridization of DNA probes.

The methods according to the present invention prevent having a loss in the upper range of the luminometer when attempting to resolve a sample of low concentration and intensity above zero. Under these conditions, the luminometer gain is typically increased to high voltages. When the luminometer gain is increased, the upper end intensity samples (high concentration of analyte) may be over-range. With the method according to the invention, the over-range values may be determined without losing any data and without repeating the measurement or the experiment.

Assay development is accelerated by the simplicity and versatility of the technique. Both immunoassay and DNA probe assay detection use common instrumentation and very similar assay formats. The technique is easily adaptable to the measurement of both large and small analytes with both high sensitivity and wide dynamic range. Assays can be formatted as either separation or nonseparation assays.

The detection is rapid, requiring only a few seconds for quantification.

Finally, the instrumentation required is not complicated, and there are no unique constraints on the disposable portions of the assay; these properties allow the rapid development of automated instruments for both the clinical immunoassay and DNA probe assay markets.

SPECIFIC DESCRIPTION OF THE INVENTION

The present invention comprises a method for detecting an electrochemiluminescent compound by inducing a luminophore to luminescence by directing an electrical waveform into the luminophore, wherein the luminescence is modulated. In a preferred embodiment of the invention, the luminescence is modulated by directing a first predetermined electrical waveform into the luminophore, followed by directing at least one subsequent pre-determined electrical waveform into the luminophore, and wherein the voltage of the subsequent waveform is less than the voltage of the first electrical waveform.

The present invention also comprises a method for measuring electrochemiluminescence comprising providing a first pulse which produces a first light intensity and a second pulse which provides a second light intensity, wherein the second light intensity is lower than the first light intensity.

In accordance with the present invention, if a sample intensity is over-range (e.g., saturation of the luminometer), the level of intensity value can be determined by means of one or more subsequent voltage pulses and a Gain Extension Factor (GEF). By generating a second pulse and determining the GEF, off-scale values from the first pulse can be determined, and the run will not need to be repeated.

In accordance with a preferred embodiment of the present invention, an ECL technique uses at least two (or more) pulses for each sample. The pulses can be either ramp or step voltage waveforms. A ramp or triangular waveform refers to applying voltage from an initial or pre-operative (POP) voltage to the upper potential at a specified scan rate. The scan rate in units of mV/sec determines the time to reach the upper potential. Slowing the scan rate will in turn slow the time it takes to reach the specified potential. To specify a ramp waveform, it will be appreciated that the initial voltage, the final voltage, and the rate must be given.

A step potential is a square waveform, and is generated by stepping the voltage directly from the POP to the desired potential, and holding it constant at that interval for a specified time interval. This time interval is referred to as the duration of the step voltage waveform. To specify a step, it will be appreciated that the initial voltage, the final voltage, and the duration must be given.

In accordance with the invention, it will be appreciated that the second or subsequent pulses are lower than the first pulse. As used herein, having a second pulse lower than the first pulse refers to having a second pulse that does not produce an off-scale reading. One skilled in the art will appreciate that the amount of luminescence, and therefore the respective ratio of the first pulse to the second pulse, is an amount that varies according to the specific design of the ECL cell, the specific luminophore, the specific luminometer, among other factors that contribute to the amount of luminescence. In accordance with the invention, the second pulse should be sufficiently lower than the first so that the second pulse is not off-scale as well. For example, using a first pulse to second pulse ratio of 100:1 has been shown effective. The exemplary 100:1 ratio was chosen so that an increase in the dynamic range of the luminometer by about two orders of magnitude (to about $10^9$ counts) could be expected. It is intended that the invention is not to be limited by the exact ratio between the first pulse and the second pulse.

In accordance with the invention, if the sample intensity during the first pulse is over-range, the lower intensity from the second pulse, being on scale, may be used to determine what the first pulse intensity would have been had it not exceeded the functional capability of the luminometer.

In accordance with the invention, the detection range of the luminometer may be increased. For example, if the scale of a particular luminometer is 1 to $10^7$ counts and the second pulse generates an intensity of exactly $10^7$ counts, if the gain extension factor is 100/1, then the first pulse would have generated $10^9$ counts had the pulse not been off-scale (higher than the $10^7$ count limit of the luminometer).

Thus, using a method according to the invention, the effective range of a luminometer is significantly increased, e.g., by 100 times, thus providing the ability to determine samples 100 times greater in intensity.

The methods according to the invention rely in part upon a consistent relationship for the ECL intensity between the first and the second pulse. If the first pulse is over-range, the extent of the over-range can be determined by knowing the second pulse and the gain extension factor (GEF) obtained from calibrating/standardizing the equipment.

As is shown in more detail in the Examples, the consistent relationship between ECL intensity of the first pulse and the ECL intensity of one or more subsequent pulses, e.g., a second pulse, refers to the ratio between the pulses at each concentration of the luminophore of interest. The ratio of intensity between the first and second pulse is termed gain extension factor (GEF). The GEF ratio is typically within a linear region of the assay in terms of the concentration of both pulses. Within this linear region where the plotted lines are parallel with equivalent slopes, the ratio should be constant. The consistency is demonstrated in the examples.

As used herein, substance or analyte of interest refers to any chemical or biological of interest that can be detected and or analyzed by electrochemiluminescence. The term includes, but is not limited to: chemicals, biologics, proteins, antibodies and their fragments, haptens, nucleic acids and their fragments, amino acids and their fragments, any one of a binding pair used in an immunoassay. For example, the systems and devices of the present invention may be particularly useful for detecting and measuring trace elements and/or pollutants, typically as metabolites for disease detection and for environmental control.

As used herein, luminophore or ECL compound refers to any molecule that produces infrared radiation, ultraviolet radiation, or visible light as a product of a chemiluminescent reaction. The luminophore is itself capable of producing a detectable chemiluminescent reaction or signal, or includes at least one indicator component that is capable of producing a detectable chemiluminescent reaction or signal. The signal, in some embodiments of the invention, may be dependent on the amount of substance in a sample. Exemplary luminophores include, but are not limited to luminol, ruthenium tris (2,2'-bipyridine) dichloride hexahydrate [Ru(bpy)$_3$Cl$_2$•6H$_2$O], or Ru(bpy)$_3^{2+}$. The present invention also includes complexes incorporating a luminophore.

As used herein, a luminometer is any device capable of detecting a luminophore, including but not limited to any photo-sensitive reading means. The methods of the present invention are applicable to all instruments and all assays using ECL detection methods.

As used herein, Gain Extension Factor (GEF) refers to the ratio of the first pulse to the second pulse. If a particular ECL system includes multiple calibrators, the GEF ratio is the average ratio for all of the calibrators.

In accordance with the invention, the GEF may be determined during the ECL cell calibration process. For example, it is conventional to calibrate or standardize the device prior to running an assay. During calibration, the device is adjusted against a reference sample. In a preferred embodiment of the invention, the GEF is determined against the reference sample, and may then be applied to the sample of interest.

For example, when an assay is run, the operator first runs a corresponding pre-determined standard reference curve over the detectable range of concentrations. In an assay where the sample(s) are run and the ECL values are on-scale based on that particular ECL intensity value, the concentration of the analyte of interest may be determined directly from the standard curve.

Similarly, in an assay where the sample(s) are run and the ECL values are off-scale based on that particular ECL intensity value, the concentration of the analyte of interest may be determined by knowing the GEF ratio and the second pulse ratio, as noted above. From the standard curve (i.e., first pulse intensity versus concentration during calibration), the concentration for an off-scale analyte of interest can be derived.

Alternatively, one long pulse could be used instead of two pulses. In this embodiment of the invention, the decay profile of the luminophore provides guidance in determining the length of the long pulse. After sufficient time, an over-ranged intensity will decay into range. By knowing the decay profile, the over-ranged intensity can be determined. For example, for this embodiment of the invention, it will be appreciated by one skilled in the art that one must determine the exponential equation for the rate of decay as the calibration curve. From the exponential equation of that line, an over-range value can be approximated. Alternatively, when an off-scale value is generated, multiple pulses can be generated until one or more on-scale values are obtained. Subsequently, from the pre-determined calibration curve (the exponential equation for the rate of decay) for that particular assay, the over-range value can be determined by measuring the amount of intensity for the first pulse between the over-range value and the calibration curve.

As used herein, it may be important to distinguish between real calibration and standardization. Calibration refers to knowledge of the absolute efficiency of the system (taking into account the optics and geometry of the sample as well as the sample chamber and the optics, geometry and efficiency of the director. Standardization refers to a method for knowing how an instrument is performing day-to-day and how its performance relates to other luminometers. ... so-called light standards . . . They are usually in the form of liquid scintillation solutions spiked with $^3H$ or $^{14}C$ and are suitable for checking that the instrument is performing consistently. Bioluminescence and chemiluminescence is made up of single photons of light produced randomly in time. It should be noted that scintillations on the other hand are made up from a burst of photons numbering two to a few hundred. The photons are produced so closely together in time that the photomultiplier will react to them en masse and produce only one pulse per scintillation and the height of that pulse will be dependent on the number of photons in the scintillation.

Methods according to the present invention are applicable to all types of excitation methods, such as those with co-reactants (oxidative-reduction or reductive-oxidation) or those without co-reactants (double potential step). These methods have been described in Leland, J. and Powell, M., *J. Electrochem. Soc.*, 137:3127 (1990); Ege, D., et al., *Anal. Chem.*, 56:2413 (1984); and Keszthelyi, C. P. and Bard, A. J., *J. Electrochem. Soc.*, 120:241 (1973).

Methods according to the present invention are also applicable to all types of ECL systems and protocols. A typical ECL system includes a potentiostat or similar device for driving the electrochemical cell and for applying a pre-determined voltage waveform; and magnet and motor control in embodiments of the invention that involve placing a permanent magnet under the cell to capture luminophore-bound magnetic beads from a flowing fluid stream; fluidics, or conduits and the like for passing the sample solution through the cell, including a peristaltic pump or the like, and valves or the like for controlling fluid flow or the direction of flow; and a sample carousel for loading multiple samples (typically 50 or more), and drawing the samples through an autopipetter into the fluidics pathway. The typical ECL system also includes a luminometer, typically including a transducer that converts light signals to electrical signals, typically a PMT; a high voltage supply to drive the PMT; and the luminometer to process the electrical signals from the PMT.

EXAMPLES

For all ECL measurements, an Origen® I analyzer (IGEN, Inc., Rockville, Md. 20852) was used. The instrument integrates a luminometer, potentiostat, electrochemical flow cell, fluid-handling components, and a 50-tube carousel. The instrument is controlled by a microcomputer via operator manipulation of on-screen menus. All immunoassays can be performed by using only minor variations on the following procedure: mix 100 µL of sample, 75 µL of coated microparticles, and 75 µL of labeled antibody, and incubate with agitation for 15 min. For a nonseparation format, insert the mixture directly into the Origen I analyzer and measure the ECL. For separation assay formats, wash the microparticles by using magnetic separation before inserting them into the analyzer.

Example 1

Figure 1A:
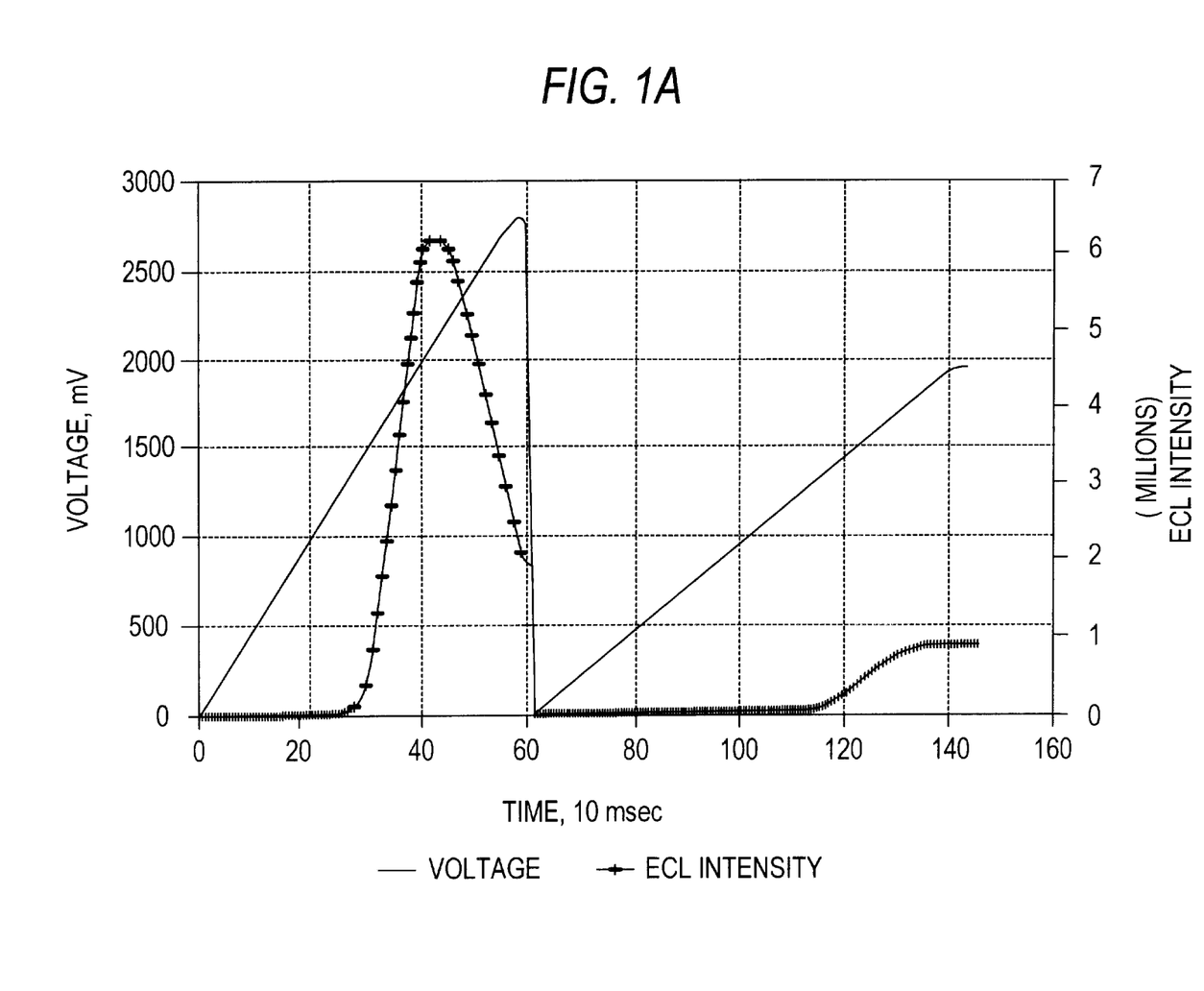
FIG. 1A is a graphic illustration of ECL intensity in response to a ramp waveform with two pulses, in accordance with an embodiment of the invention.
Figure 1B:
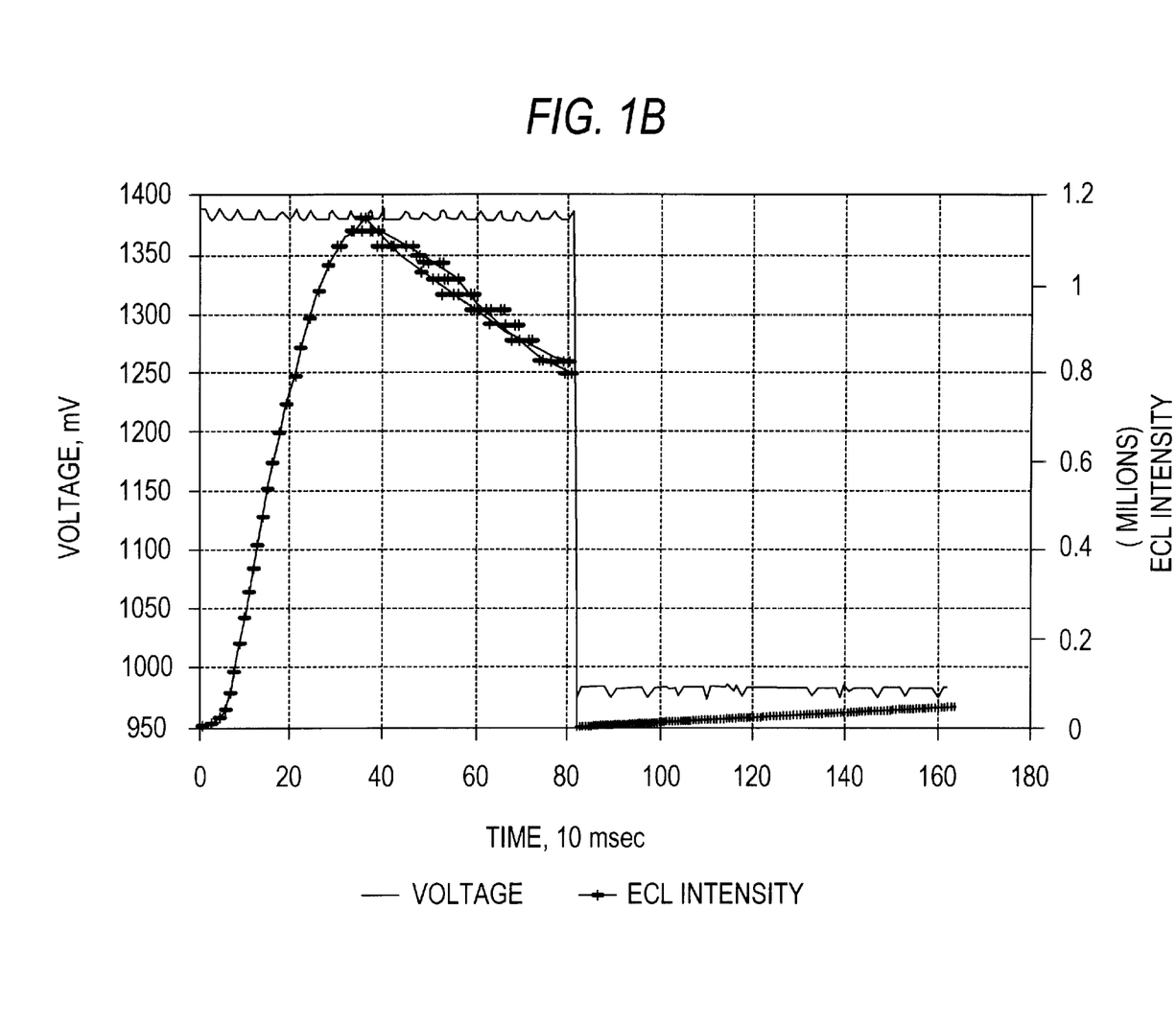
FIG. 1B is a graphic illustration of ECL intensity in response to a step waveform with two pulses, in accordance with an embodiment of the invention.

In this work, the pulses were set up to give GEF's of about 100. For the ramp voltage waveform, the second pulse is generated at both a lower scan rate and a lower voltage than the first pulse. See FIGS. 1A and 1B.

Example 2

For each assay the Gain Extension Factor (GEF) must be determined. The determination is made while running control standards for the calibration assay using the two-pulse format. The ORIGEN® I Analyzer is programmed to automatically subtract the first pulse assay buffer reading (background) from all subsequent first pulse values, and then subtract the second pulse assay buffer reading (background) from all subsequent second pulse values. After correcting for background, each calibrator's first and second pulse values are measured.

The GEF ratio is then calculated by taking the ratio of the first pulse to the second pulse and averaged over each calibrator. This GEF value will then be used in future assays to calculate off-scale values.

Example 3

The method of determining the off-scale values requires two steps. First, the Gain Extension Factor (GEF) must be determined for the specific assay. This is accomplished by means of a standard calibration curve where two pulses are generated for each calibrator. After correcting for background, the average GEF for the assay is calculated by taking the ratio of the first pulse to the second pulse for each calibrator. For each assay the GEF may be different, making this value assay-dependent. Assay-dependent means that for each type of assay, a calibration assay to determine the GEF must be generated. The GEF is measured each time the assay is re-standardized. The GEF stability is as good as the stability of the assay. Once the GEF for the specific assay has been determined, this value is then used to calculate over-ranged readings in future assays.

Example 4

Figure 2:
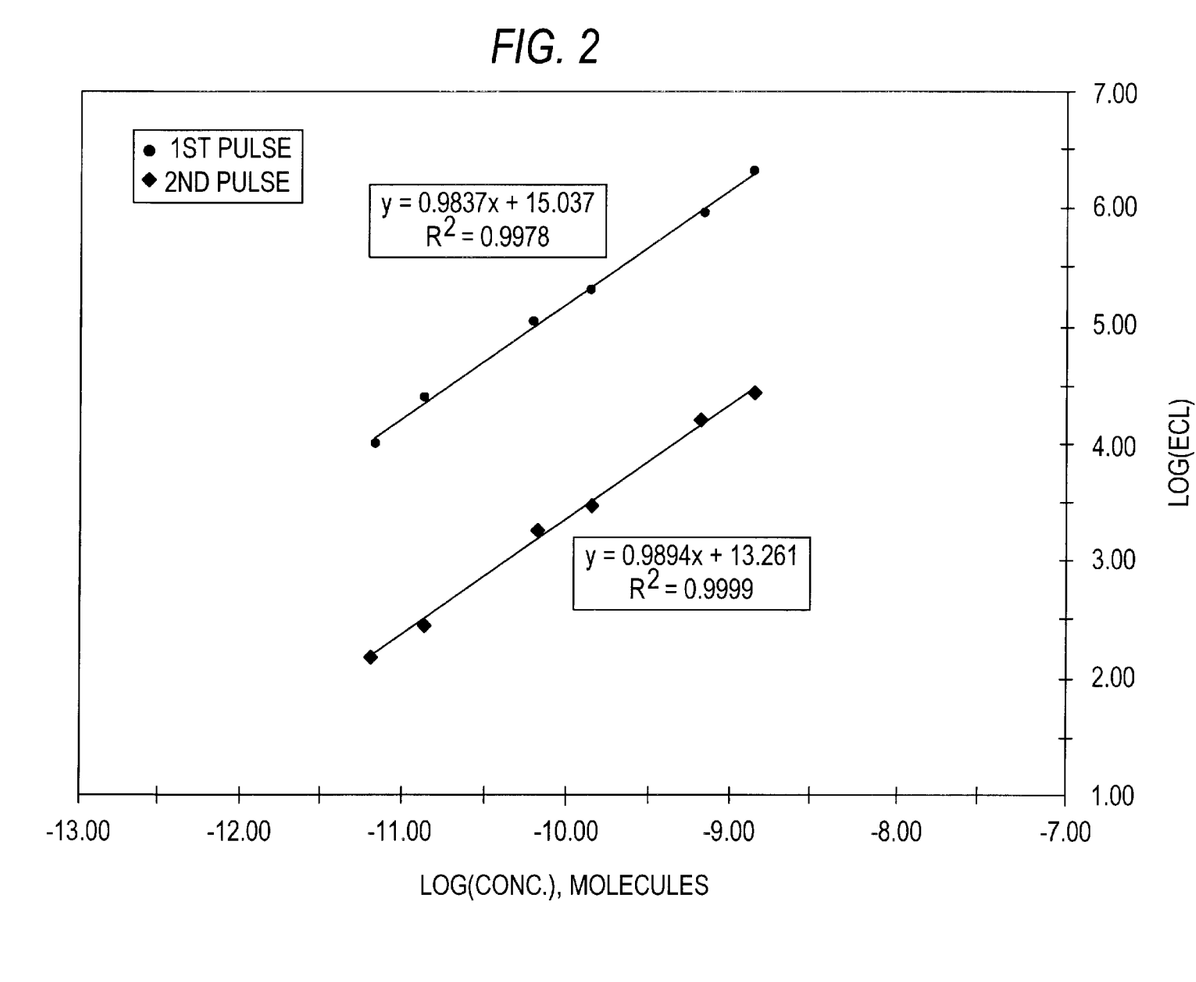
FIG. 2 is an exemplary calibration curve using a ramp voltage waveform for deriving the gain extension factor for a prostate surface antigen assay.
Figure 3:
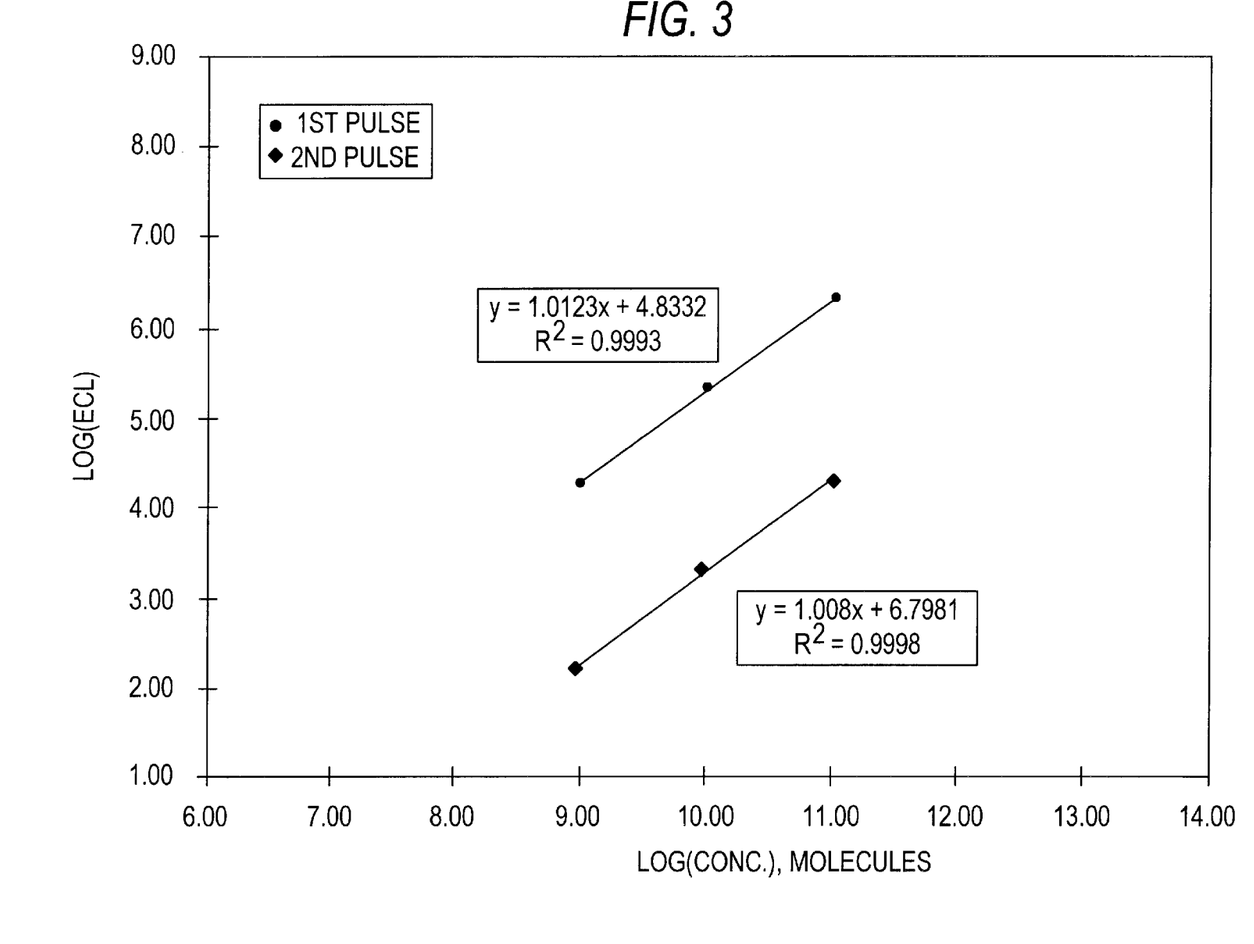
FIG. 3 is an exemplary calibration curve using a step potential waveform for deriving the gain extension factor for a lambda DNA assay.

To validate the luminometer scale extension method, two different assays, prostate surface antigen (PSA) and λDNA, were tested. The protocol for setting up the experiment was similar for both assays as described below:

1. Calibration: A calibration curve for each assay is first established using only those calibrators within a linear range. Once the assay reagents are prepared according to the standard protocol, each assay is run with each sample being pulsed twice, as previously described. The PSA assay was run using the ramp voltage waveform, and the Lambda DNA assay was run using the step potential waveform. Once the values have been corrected for background, two linear curves (one from each pulse) should be obtained (having a slope of 1.0 on log-log scale). See FIGS. 2 and 3. From these two curves, a mean Gain Extension Factor (GEF) value is obtained by taking a ratio of the first pulse of the calibrators to the second pulse of the calibrators. This GEF will be used to approximate the off-scale values in subsequent assays.

Figure 4:
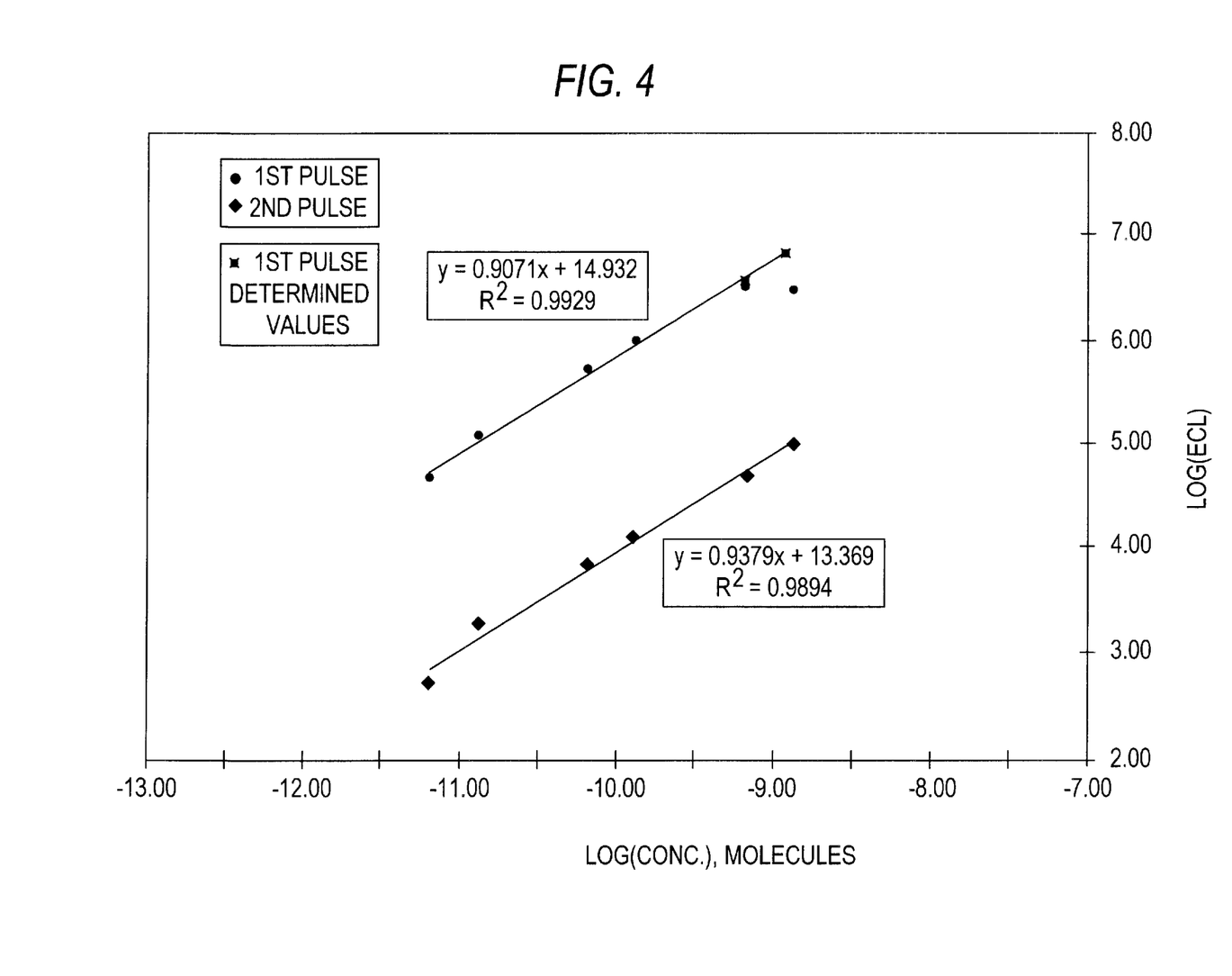
FIG. 4 is the exemplary off-scale value determination using the gain extension factor shown in FIG. 2.
Figure 5:
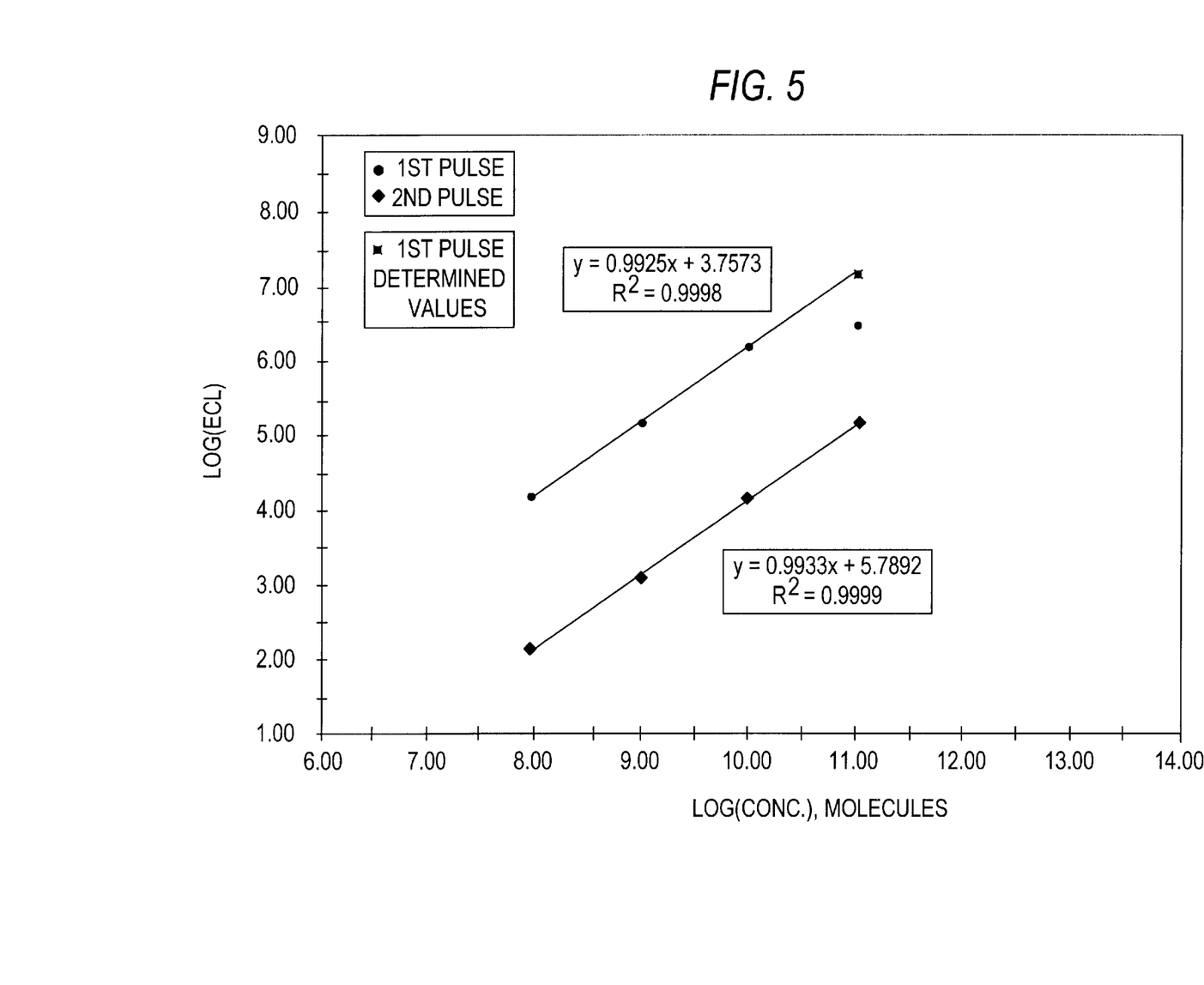
FIG. 5 is the exemplary off-scale value determination using the gain extension factor shown in FIG. 3.

2. Assay with Over-Ranged Values: An assay, in which the highest calibrator(s) over-ranged, was run by increasing the photomultiplier tube (PMT) gain. The same protocol used in the calibration assay is used, including pulsing each sample twice. The off-scale readings can then be determined by multiplying the second pulse intensity by the GEF obtained in the calibration assay. These values are compared to the expected values. How well the calculated values fall on the calibration line indicates the overall performance of the method. The results are shown in FIGS. 4 and 5. The method was successful for both the PSA assay and the λDNA assay. Using the GEF and second pulse values, reasonable values were obtained for all off-scale readings. Using the method, the luminometer's range can be extended as much as two orders of magnitude. For example, the ORIGEN analyzer's luminometer range is 1 to $10^7$. With this method, the range is increased to 1 to $10^9$.

Subsequently, when the assay is run and an off-scale reading occurs, a second pulse will be generated for the saturated sample. The off-scale reading can then be approximated by multiplying the second pulse value by the GEF obtained in the calibration assay.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. An ECL detection method comprising the steps of:

determining a gain extension factor for an assay;

applying a first electrical excitation signal to an assay sample to induce a first ECL emission having a first intensity;

determining whether said first intensity is outside an operational range of a light detector; and, if said first intensity is outside said operational range, then:

applying a second electrical excitation signal to said assay sample to induce a second ECL emission having a second intensity within said operational range; and determining an ECL intensity value for said first intensity as a function of said gain extension factor and of said second intensity.

2. The ECL detection method according to claim 1, wherein the step of determining a gain extension factor comprises the steps of:

applying said first electrical excitation signal to a reference sample to induce a third ECL emission having a third intensity within a first operational range of said light detector;

applying said second electrical excitation signal to said reference sample to induce a fourth ECL emission having a fourth intensity within a second operational range of said light detector; and determining said gain extension factor as a function of said third intensity and of said fourth intensity.

3. The ECL detection method according to claim 2, wherein the step of determining said gain extension factor comprises the step of calculating said gain extension factor as a ratio of said third intensity and of said fourth intensity.

4. The ECL detection method according to claim 2, wherein said first operational range is substantially equivalent to said second operational range.

5. The ECL detection method according to claim 1, wherein a peak voltage of said second electrical excitation signal is less than a peak voltage of said first electrical excitation signal.

6. The ECL detection method according to claim 1, wherein a period of said second electrical excitation signal is longer than a period of said first electrical excitation signal.

7. The ECL detection method according to claim 1, wherein said first electrical excitation signal comprises a first pulse signal and wherein said second electrical excitation signal comprises a second pulse signal.

8. The ECL detection method according to claim 1, wherein said first intensity is greater than said second intensity.

9. The ECL detection method according to claim 1, wherein said first intensity is less than said second intensity.

10. An ECL detection method comprising the steps of:

determining a gain extension factor for an assay;

applying a first electrical excitation signal to an assay sample to induce a first ECL emission having a first intensity;

determining whether said first intensity is outside an operational range of a light detector; and, if said first intensity is outside said operational range, then:

adjusting a gain of said light detector to produce an adjusted operational range of said light detector;

applying a second electrical excitation signal to said assay sample to induce a second ECL emission having a second intensity within said adjusted operational range of said light detector; and determining an ECL intensity value for said first intensity as a function of said gain extension factor and of said second intensity.

11. The ECL detection method according to claim 10, wherein the step of determining a gain extension factor comprises the steps of:

applying said first electrical excitation signal to a reference sample to induce a third ECL emission having a third intensity within a first operational range of said light detector;

applying said second electrical excitation signal to said reference sample to induce a fourth ECL emission having a fourth intensity within a second operational range of said light detector; and determining said gain extension factor as a function of said third intensity and of said fourth intensity.

12. The ECL detection method according to claim 11, wherein the step of determining said gain extension factor comprises the step of calculating said gain extension factor as a ratio of said third intensity and of said fourth intensity.

13. The ECL detection method according to claim 11, wherein said first operational range is not substantially equivalent to said second operational range.

14. The ECL detection method according to claim 10, wherein a peak voltage of said second electrical excitation signal is less than a peak voltage of said first electrical excitation signal.

15. The ECL detection method according to claim 10, wherein a period of said second electrical excitation signal is longer than a period of said first electrical excitation signal.

16. The ECL detection method according to claim 10, wherein said first electrical excitation signal comprises a first pulse signal and wherein said second electrical excitation signal comprises a second pulse signal.

17. The ECL detection method according to claim 10, wherein said first intensity is greater than said second intensity.

18. The ECL detection method according to claim 10, wherein said first intensity is less than said second intensity.

19. An ECL detection method comprising the steps of:

determining a gain extension factor for an assay;

applying a first electrical excitation signal to an assay sample to induce a first ECL emission having a first intensity;

determining whether said first intensity exceeds an operational range of a light detector; and, if said first intensity exceeds said operational range, then:

applying a second electrical excitation signal to said assay sample to induce a second ECL emission having a second intensity within said operational range of said light detector; and determining an analyte concentration within said assay sample as a function of said gain extension factor and of said second intensity.

20. The ECL detection method according to claim 19, wherein the step of determining a gain extension factor comprises the steps of:

applying said first electrical excitation signal to a reference sample to induce a third ECL emission having a third intensity within a first operational range of said light detector;

applying said second electrical excitation signal to said reference sample to induce a fourth ECL emission having a fourth intensity within a second operational range of said light detector; and determining said gain extension factor as a function of said third intensity and of said fourth intensity.

21. The ECL detection method according to claim 20, wherein the step of determining said gain extension factor comprises the step of calculating said gain extension factor as a ratio of said third intensity and of said fourth intensity.

22. The ECL detection method according to claim 20, wherein said first operational range is not substantially equivalent to said second operational range.

23. The ECL detection method according to claim 19, wherein a peak voltage of said second electrical excitation signal is less than a peak voltage of said first electrical excitation signal.

24. The ECL detection method according to claim 19, wherein a period of said second electrical excitation signal is longer than a period of said first electrical excitation signal.

25. The ECL detection method according to claim 19, wherein said first electrical excitation signal comprises a first pulse signal and wherein said second electrical excitation signal comprises a second pulse signal.

26. The ECL detection method according to claim 19, wherein said first intensity is greater than said second intensity.

27. The ECL detection method according to claim 19, wherein said first intensity is less than said second intensity.

28. An ECL detection method comprising the steps of:

determining a gain extension factor for an assay;

applying a first electrical excitation signal to an assay sample to induce a first ECL emission having a first intensity;

applying a second electrical excitation signal to said assay sample to induce a second ECL emission having a second intensity;

determining whether said first intensity is outside an operational range of a light detector; and, if said first intensity is outside said operational range, then:

determining an ECL intensity value for said first intensity as a function of said gain extension factor and of said second intensity.

29. The ECL detection method according to claim 21, wherein the step of determining a gain extension factor comprises the steps of:

applying said first electrical excitation signal to a reference sample to induce a third ECL emission having a third intensity within a first operational range of said light detector;

applying said second electrical excitation signal to said reference sample to induce a fourth ECL emission having a fourth intensity within a second operational range of said light detector; and determining said gain extension factor as a function of said third intensity and of said fourth intensity.

30. The ECL detection method according to claim 29, wherein the step of determining said gain extension factor comprises the step of calculating said gain extension factor as a ratio of said third intensity and of said fourth intensity.

31. The ECL detection method according to claim 29, wherein said first operational range is substantially equivalent to said second operational range.

32. The ECL detection method according to claim 28, wherein a peak voltage ,of said second electrical excitation signal is less than a peak voltage of said first electrical excitation signal.

33. The ECL detection method according to claim 28, wherein a period of said second electrical excitation signal is longer than a period of said first electrical excitation signal.

34. The ECL detection method according to claim 28, wherein said first electrical excitation signal comprises a first pulse signal and wherein said second electrical excitation signal comprises a second pulse signal.

35. The ECL detection method according to claim 28, wherein said first intensity is greater than said second intensity.

36. The ECL detection method according to claim 28, wherein said first intensity is less than said second intensity.

37. An ECL detection method comprising the steps of:

determining a gain extension factor for an assay;

applying a first electrical excitation signal to an assay sample to induce a first ECL emission having a first intensity;

applying a second electrical excitation signal to said assay sample to induce a second ECL emission having a second intensity;

determining whether said first intensity is outside an operational range of a light detector; and, if said first intensity is outside said operational range, then:

determining an analyte concentration within said assay sample as a function of said gain extension factor and of said second intensity.

38. The ECL detection method according to claim 37, wherein the step of determining a gain extension factor comprises the steps of:

applying said first electrical excitation signal to a reference sample to induce a third ECL emission having a third intensity within a first operational range of said light detector;

applying said second electrical excitation signal to said reference sample to induce a fourth ECL emission having a fourth intensity within a second operational range of said light detector; and determining said gain extension factor as a function of said third intensity and of said fourth intensity.

39. The ECL detection method according to claim 38, wherein the step of determining said gain extension factor comprises the step of calculating said gain extension factor as a ratio of said third intensity and of said fourth intensity.

40. The ECL detection method according to claim 38, wherein said first operational range is not substantially equivalent to said second operational range.

41. The ECL detection method according to claim 37, wherein a peak voltage of said second electrical excitation signal is less than a peak voltage of said first electrical excitation signal.

42. The ECL detection method according to claim 37, wherein a period of said second electrical excitation signal is longer than a period of said first electrical excitation signal.

43. The ECL detection method according to claim 37, wherein said first electrical excitation signal comprises a first pulse signal and wherein said second electrical excitation signal comprises a second pulse signal.

44. The ECL detection method according to claim 37, wherein said first intensity is greater than said second intensity.

45. The ECL detection method according to claim 37, wherein said first intensity is less than said second intensity.

46. An ECL detection method comprising the steps of:

determining a gain extension factor for an assay;

applying a first electrical excitation signal to an assay sample to induce a first ECL emission having a first intensity;

detecting said first ECL emission with a light detector having a first gain;

adjusting said light detector to have a second gain and to produce an adjusted operational range of said light detector;

applying a second electrical excitation signal to said assay sample to induce a second ECL emission having a second intensity;

detecting said second ECL emission with said light detector;

determining whether said first intensity is outside an operational range of said light detector; and, if said first intensity is outside said operational range, then:

determining an ECL intensity value for said first intensity as a function of said gain extension factor, said first gain, said second gain and said second intensity.

47. An ECL detection method comprising the steps of:

applying an electrical excitation signal to an assay sample to induce an ECL emission having a first intensity at a first time and having a second intensity at a second time;

detecting said first intensity with a light detector having an operational range;

before said second time, adjusting a gain of said light detector to produce an adjusted operational range of said light detector wherein said second intensity is within said adjusted operational range; and determining an ECL intensity value as a function of said second intensity and said gain.

48. The ECL detection method according to claim 47, wherein the step of adjusting a gain comprises the step of predicting said second intensity as a function of said first intensity and said operational range.

49. The ECL detection method according to claim 47, wherein said electrical excitation signal comprises a ramp signal.

50. The ECL detection method according to claim 47, wherein said electrical excitation signal comprises a plurality of pulse signals.

\* \* \* \* \*